(12) United States Patent
King et al.

(10) Patent No.: US 7,291,348 B2
(45) Date of Patent: Nov. 6, 2007

(54) COMPOSITIONS AND METHODS FOR BIODEGRADABLE MICROSPHERES AS CARRIERS OF BIOACTIVE SUBSTANCES

(75) Inventors: Timothy W. King, Englewood Cliffs, NJ (US); Charles W. Patrick, Jr., Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/187,505

(22) Filed: Jul. 22, 2005

(65) Prior Publication Data

US 2005/0255165 A1 Nov. 17, 2005

Related U.S. Application Data

(62) Division of application No. 09/671,540, filed on Sep. 27, 2000, now Pat. No. 6,962,716.

(51) Int. Cl.
*A61K 9/14* (2006.01)
*A61K 9/50* (2006.01)
*B01J 13/02* (2006.01)

(52) U.S. Cl. ............... 424/489; 424/501; 424/502; 427/213.31; 427/213.36; 428/402.21

(58) Field of Classification Search ........... 424/489, 424/501, 502
See application file for complete search history.

(56) References Cited

U.S. PATENT DOCUMENTS 5,407,609 A 4/1995 Tice et al.

(Continued)

FOREIGN PATENT DOCUMENTS

| EP | 1180548 A | 2/2002 |
|---|---|---|
| WO | WO 9317126 A | 9/1993 |
| WO | WO 0142512 A | 6/2001 |
| WO | WO 0171039 A | 9/2001 |

OTHER PUBLICATIONS

Putney, et al, "Improving protein therapeutics with sustained-release formulations," Dec. 1997, Nature Biotechnology, vol. 16, Feb. 1998, pp. 153-157.

(Continued)

*Primary Examiner*—Carlos A. Azpuru
(74) *Attorney, Agent, or Firm*—Gardere Wynne Sewell LLP

(57) ABSTRACT

A cost-effective, scalable technique for producing microspheres loaded with biologically active solid proteins is provided. The microspheres degrade over time and release biologically active VEGF, as demonstrated by the proliferation of HUVECs in vitro compared to negative controls. A defined concentration of microspheres can deliver a quantifiable level of VEGF with known release kinetics. The invention can be used with other growth factors and applied to tissue engineering applications such as the regeneration of peripheral nerve, bone, adipose tissue, and solid organs. The method of the invention includes the steps of dissolving a polymer with an organic solvent to produce a polymer solution; adding a biologically effective amount of a bioactive substance to the solution to produce a mixture of the polymer and the bioactive substance; vibrating the mixture to produce a bioactive substance-polymer complex; emulsifying the mixture to produce an emulsion comprising the bioactive substance-polymer complex; and extracting the organic solvent from the emulsion to produce microspheres comprising the polymer-bioactive substance complex, wherein the bioactivity of the bioactive substance is usefully preserved.

6 Claims, 6 Drawing Sheets

U.S. PATENT DOCUMENTS

| | | |
|---|---|---|
| 5,410,016 A | 4/1995 | Hubbell et al. |
| 5,462,990 A | 10/1995 | Hubbell et al. |
| 5,560,438 A | 10/1996 | Collee et al. |
| 5,573,934 A | 11/1996 | Hubbell et al. |
| 5,622,657 A | 4/1997 | Takada et al. |
| 5,626,863 A | 5/1997 | Hubbell et al. |
| 5,643,605 A | 7/1997 | Cleland et al. |
| 5,795,714 A | 8/1998 | Canter et al. |
| 5,858,746 A | 1/1999 | Hubbell et al. |
| 5,869,041 A | 2/1999 | Vandenburgh |
| 5,912,015 A | 6/1999 | Bernstein et al. |
| 5,916,597 A | 6/1999 | Lee et al. |
| 5,919,626 A | 7/1999 | Shi et al. |
| 6,013,449 A | 1/2000 | Hacia et al. |
| 6,123,956 A | 9/2000 | Baker et al. |

OTHER PUBLICATIONS

King, Timothy W., et al., "Development and in vitro characterization of vascular endothelial growth factor (VEGF)-loaded poly(DL-lactic-co-glycolic acid)/poly(ethylene glycol) microspheres using a solid encapsulation/single emulsion/solvent extraction technique," Dec. 30, 1999, J Biomed. Mater. Res., Sep. 2000; 51 (3):383-390.

Xudong Cao, et al, "Delivering neuroactive molecules from biodegradable microshphers for application in central nervous system disorders," Jul. 16, 1998, Biomaterials 20 (1999) 329-339.

Bulyk, et al, "Quantifying DNA-protein interactions by double-stranded DNA arrays," Nature Biotechnology, Nature Publishing, US, vol. 17, Jun. 1999, pp. 573-577.

Duggan, et al., "Expression profiling using CDNA microarrays," Nature Genetics, New York, NY, US, vol. 21, no. Suppl, Jan. 1999, pp. 10-14.

COMPOSITIONS AND METHODS FOR BIODEGRADABLE MICROSPHERES AS CARRIERS OF BIOACTIVE SUBSTANCES

CROSS REFERENCE TO RELATED APPLICATIONS

This application is a divisional of U.S. patent application Ser. No. 09/671,540 filed on Sep. 27, 2000 now U.S. Pat. No. 6,962,716.

FIELD OF THE INVENTION

The present invention relates generally to the field of microencapsulation and, in particular, to compositions and methods for the fabrication of biodegradable microspheres and their use as delivery vehicles for bioactive substances such as solid proteins.

BACKGROUND OF THE INVENTION

Without limiting the scope of the invention, its background is described in connection with tissue engineering and angiogenesis as an example. Further, for purposes of the ensuing discussion, description and claims of the present invention, the terms "protein", "polypeptide" and "peptide" may be used interchangeably, although it will be appreciated by those skilled in the art that biological distinctions may be drawn between them and, as such distinctions do not affect the operation of the present invention, such distinctions as may be drawn are contemplated by the scope of the present invention.

The advent of recombinant DNA and protein technology makes possible the production of significant quantities of both DNA and proteins for use in the clinical setting. The appeal of recombinant therapeutics is enhanced by delivery systems that provide controlled pharmacokinetics of the desired therapy. Paramount to the development of such a delivery system is the assurance that the biological activity of the material is preserved throughout manufacturing, storage, delivery, and release. Biodegradable microspheres have the potential to meet these requirements.

Methods are known to encapsulate various proteins within biodegradable microspheres. In particular, polypeptides have been incorporated into Poly(DL-lactide-co-glycolide) (PLGA) microspheres with varying degrees of success. PLGA is a polymer that has been used for many years as a biodegradable suture material. PLGA is biocompatible and degrades by hydrolytic cleavage into nontoxic molecules that are easily eliminated from the body (namely, lactic acid and glycolic acid). In addition to polypeptide microencapsulation, sustained delivery of polypeptides is also possible through the use of biodegradable microspheres. A non-exhaustive list of such polypeptides includes nerve growth factor, alpha, beta and gamma interferon, growth hormone, insulin erythropoietin, transforming growth factor beta, epidermal growth factor interleukin-2, basic fibroblast growth factor and vascular endothelial growth factor. PLGA has been described, therefore, as a desirable polymer for use as a drug delivery system. Preserving the biological activity of the microencapsulated polypeptide, however, has proven to be problematic and has retarded the development of microencapsulation drug delivery.

The double-emulsion technique is the most commonly reported method for manufacturing microspheres. According to this technique, protein dissolved in an aqueous solution is then emulsified in an organic solvent containing the dissolved PLGA. The aqueous-organic emulsion is then further emulsified in an aqueous alcohol phase to create an aqueous-organic-aqueous double emulsion. The alcohol phase extracts the organic solvent away from the PLGA in approximately one hour, leaving the protein entrapped in discrete droplets within solid microspheres. The process of emulsifying the aqueous protein solution in the organic solvent, however, can easily denature the protein.

Protein may be encapsulated into microspheres by known methods either in solution or as a solid. The incorporation of solid protein into a microsphere has previously been accomplished by the atomization-freeze (AF) process. The AF process requires the use of an ultrasonic atomizer with a custom designed spray nozzle. A description of the atomization-freeze technique is found in Putney S. D., Burke P. A., "Improving Protein Therapeutics with Sustained-release Formulations," Nat. Biotechnol 1998; 16:153-157.

Another method for the encapsulation of solid proteins is described in Cao X., Schoichiet M. S., "Delivering Neuroactive Molecules from Biodegradable Microspheres for Application in Central Nervous System Disorders," Biomaterials 1999; 20:329-339. Briefly, Cao and Schoichet dispersed ovalbumin powder in a solution of PLGA in chloroform using a Polytron homogenizer. The protein-polymer dispersion was added to an aqueous solution of 1% polyvinyl alcohol (PVA) and homogenized again to form an emulsion. The emulsion was added to more PVA solution and stirred continuous to evaporate the organic solvent. The microspheres were centrifuged, washed and freeze dried.

One problem with the method of Cao, et al., is the use of a single polymer species such as PLGA alone, or a PLGA/poly(eta-caprolactine) to fabricate the microspheres. Certain advantages in the release kinetics of the microspheres may be achieved by using a mixture of polymers rather than a single polymer species to fabricate the microspheres. Release kinetics are determined, in part, by the amount of bioactive substances loaded, the polymer or polymers used and the conditions of manufacture. The particle size of the microspheres is determined to a large extent by the manufacturing conditions such as polymer viscosity and the method of physical shearing used to produce the microspheres. Methods of shearing include but are not limited to homogenization with a tissue homogenizer or blender, ultrasound sonication, or vibrating with the use of a VORTEX® mixer. Smaller particles have a faster rate of degradation due to the increased ratio of surface area to volume. Thus, for microspheres composed of PLGA alone, the release of protein is generally regulated only by the physical erosion of the polymer, particularly where the protein/polymer ratio of the microsphere is low. Another problem with the Cao, et al., method is the use of a tissue homogenizer to form the polymer emulsion. In terms of commercial scale-up of microsphere production, a tissue homogenizer is impractical. Homogenizers have parts such as blades, rotors and containers that require cleaning and sterilization between each batch. The care and maintenance of homogenizers renders them problematic for the large scale production of pharmaceutical microspheres.

SUMMARY OF THE INVENTION

The present invention solves the problems in the prior art just described by providing a solid-encapsulation/single-emulsion/solvent extraction technique to encapsulate solid proteins and other bioactive substances into biodegradable microspheres. The present invention provides a cost-effective, scalable technique for producing microspheres loaded with biologically active proteins, and in particular solid proteins, together with compositions of such microspheres.

One method for making microspheres of the present invention that encapsulate and effect the controlled release of a bioactive substance includes the steps of dissolving a polymer with an organic solvent to produce a polymer solution, adding a biologically effective amount of a bioactive substance to the solution to produce a mixture of the polymer and the bioactive substance, vibrating the mixture to produce a bioactive substance-polymer complex, emulsifying the mixture to produce an emulsion of the bioactive substance-polymer complex and the organic solvent, and extracting the organic solvent from the emulsion to produce microspheres comprising the polymer-bioactive substance complex, so that the bioactivity of the bioactive substance is usefully preserved.

The present invention provides a system for delivering a therapeutic agent to tissue. The system includes biodegradable microspheres made as described above and encapsulating a therapeutic agent as the bioactive substance in a dispenser for administration of the microspheres to the tissue so that the microspheres release the therapeutic agent from the microspheres to the tissue.

The present invention further provides a drug delivery system. The drug delivery system includes biodegradable microspheres incorporating a drug made as previously described and a dispenser for administration of the microspheres. The release of the therapeutic agent or the drug from the microspheres occurs in two phases: an initial burst phase and a later steady-state phase.

In addition to methods and systems, the present invention provides microsphere compositions. Microspheres of the present invention contain bioactive substances such as polypeptides, therapeutic agents or drugs. A particular feature of the present compositions is that bioactive substances in their solid state, not dissolved in solution, may be contained in the microspheres with the bioactivity of the substance preserved. Another feature of the present invention is that solid bioactive substances are incorporated into microspheres without using the atomization-freeze process familiar to those skilled in the art. Further, the present invention does not make use of a tissue homogenizer or an ultrasonic atomizer.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

Figure 1:
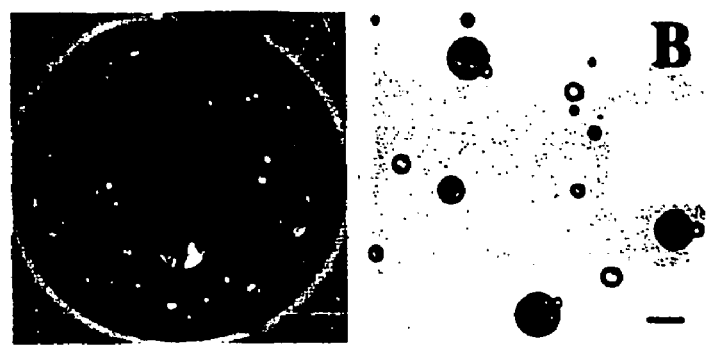
FIG. 1A is a photograph of a large microsphere of the present invention viewed by bright-field microscopy.
FIG. 1B is a photograph of a population of small microspheres of the present invention viewed by bright-field microscopy.

While the making and using of the various embodiments of the present invention are discussed in detail below, it should be appreciated that the present invention provides many applicable inventive concepts which can be embodied in a wide variety of specific contexts. The specific embodiments described herein are merely illustrative of specific ways to make and use the invention and do not delimit the scope of the invention nor the scope of the claims appended hereto.

A bioactive substance, as defined herein, is an agent, or its pharmaceutically acceptable salt, which possesses therapeutic, prophylactic or diagnostic properties in vivo or which influences the biological structure, function, or activity of a cell or tissue of a living organism. Examples of suitable therapeutic and/or prophylactic biologically active agents include, for instance, proteins such as immunoglobulin-like proteins, antibodies, cytokines (e.g., lymphokines, monokines, chemokines), interleukins, interferons, erythropoietin, nucleases, tumor necrosis factor, colony stimulating factors, immunoadjuvants, insulin, enzymes, tumor suppressors, hormones (e.g., growth hormone and adrenocorticotrophic hormone), antigens (e.g., bacterial and viral antigens), growth factors; peptides; polypeptides; proteins, nucleic acids such as antisense molecules; and small molecules such as antibiotics, steroids, decongestants, neuroactive agents, anesthetics, sedatives, anti-tumor agents, cardiovascular agents, antineoplastics, antihistamines, hormones and vitamins. Examples of suitable diagnostic and/or therapeutic bioactive agents include radioactive isotopes and radiopaque agents.

A microsphere, as defined herein, includes a particle of a biocompatible solid-phase material having a diameter of about one millimeter to about one micrometer, or less, wherein the particle may contain a biologically active agent and, wherein the solid-phase material sustains the in vivo release of the biologically active agent from the microsphere. A microsphere can have a spherical, non-spherical or irregular shape. The typical microsphere shape is generally spherical.

A biocompatible material, as defined herein, means that the material, and any degradation products of the material, is non-toxic to the recipient and also presents no significant deleterious or untoward effects on the recipient's body, such as an immunological reaction at the injection site.

Particles of a biologically active agent include, for example, crystalline particles, non-crystalline particles, freeze dried particles and lyophilized particles. The particles may contain only the biologically active agent or may also contain one or more stabilizing agents and/or other excipients.

Typically, the solid-phase material of the microsphere is a biocompatible polymer that may be either a biodegradable polymer, a non-biodegradable polymer, blends thereof or copolymers thereof.

Biodegradable, as defined herein, means the polymer will degrade or erode in vivo to form smaller chemical species. Degradation can result, for example, by enzymatic, chemical and/or physical processes. Suitable biocompatible, biodegradable polymers include, for example, poly(lactide)s, poly (glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, hydrogels, blends and copolymers thereof.

Biocompatible, non-biodegradable polymers suitable for the methods and compositions of the present invention include non-biodegradable polymers selected from the group consisting of polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, hydrogels, blends and copolymers thereof.

Further, the terminal functionalities of a polymer can be modified. For example, polyesters may be blocked, unblocked or a blend of blocked and unblocked polymers. A blocked polyester is as classically defined in the art, specifically having blocked carboxyl end groups. Generally, the blocking group is derived from the initiator of the polymerization and is typically an alkyl group. An unblocked polyester is as classically defined in the art, specifically having free carboxyl endgroups.

Acceptable molecular weights for polymers used in the present invention may be determined by a person of ordinary skill in the art accounting for factors such as the desired polymer degradation rate, physical properties such as mechanical strength and rate of dissolution of polymer in solvent. Typically, an acceptable range of molecular weights is of about 2,000 Daltons to about 2,000,000 Daltons. In one embodiment, the polymer is a biodegradable polymer or copolymer. In another embodiment, the polymer is a poly(lactide-co-glycolide) (hereinafter "PLGA") with a lactide:glycolide ratio of about 1:1 and a molecular weight of about 5,000 Daltons to about 70,000 Daltons. In yet another embodiment, the PLGA used in the present invention has a molecular weight of about 5,000 Daltons to about 42,000 Daltons.

The invention is now described in an example demonstrating the successful microencapsulation of a solid polypeptide growth factor and the controlled released of the factor to stimulate cell proliferation. Reference is made to King T. W., and Patrick, C. W., Jr., "Development and in Vitro Characterization of Vascular Endothelial Growth Factor (VEGF)-loaded Poly(dl-lactic-co-glycolic Acid)/poly(ethylene Glycol) Microspheres Using a Solid Encapsulation/single Emulsion/solvent Extraction Technique," J. Biomed. Mater. Res., September 2000; 51(3):383-390, the disclosure of which is incorporated herein by reference. Reference is also made to King, Timothy W., "Enhanced in Vivo Angiogenesis Within a Model Tissue Engineered Construct Using Biodegradable Microspheres Containing Encapsulated VEGF," Ph.D. Dissertation, The University of Texas M.D. Anderson Cancer Center and The University of Texas Graduate School of Biomedical Sciences, Houston, Tex. May, 2000, the disclosure of which is also incorporated herein by reference.

The field of tissue engineering is one application that may benefit from the development of a therapeutic delivery system. Tissue engineering techniques offer a potential means to develop autologous tissues for repair of primary tissue defects, regardless of whether the defect is a solid organ, soft tissue, or bony tissue. The appropriate regulation of angiogenesis, however, is critical to the incorporation of a vascular network into a viable engineered tissue. Vascular endothelial growth factor (VEGF) is a potent stimulator of angiogenesis. Several investigators have demonstrated the ability of VEGF to stimulate therapeutic angiogenesis in vivo. One embodiment of the present invention is a controlled-release VEGF delivery system that regulates angiogenesis within tissue-engineered constructs. To illustrate the invention, the manufacture, characterization, in vitro degradation, and bioactivity of VEGF microspheres over a 28-day course are described.

One modality of controlled delivery of biologically active molecules to a tissue is microspheres of Poly(DL-lactide-co-glycolide) (PLGA)/polyethylene glycol (PEG). Tissues to which a bioactive substance may be delivered include, but are not limited to, engineered tissue for use in plastic and reconstructive surgery. Engineered tissue requires a blood supply for the engineered tissue to successfully integrate with natural tissue and to achieve the pliability of natural tissue. Angiogenesis is the process of the growth of blood vessels into tissue to supply the tissue with blood. To stimulate angiogenesis within an engineered tissue, vascular endothelial growth factor (VEGF) and bovine serum albumin (BSA) were coencapsulated into microspheres fabricated from PEG and 50/50 PLGA using a solid-encapsulation/single-emulsion/solvent extraction technique of the present invention.

Two VEGF/BSA ratios were studied: 1:2000 and 1:10,000. The studies include analysis of the loading efficiency and particle size distribution, bright-field microscopy, scanning electron microscopy, release kinetics, and an in vitro human umbilical vein endothelial cell (HUVEC) proliferation assay to assess biological activity of the released VEGF.

The microspheres were manufactured, stored, and degraded over 28 days. The burst release rates for 1:2000 and 1:10,000 VEGF/BSA microspheres were 71.87±8.11 and 27.91±1.71 ng/mL (mean±standard error of the mean), respectively; steady-state release rates were 6.56±1.10 and 2.21±0.47 ng/mL, respectively. The microspheres released biologically active VEGF, and the VEGF increased the proliferation of HUVECs in culture ($p \leq 0.05$). The data obtained from these studies demonstrate that a defined concentration of microspheres of the invention will deliver a quantifiable level of VEGF at a known release rate.

Microsphere production

To illustrate the solid-encapsulation/single-emulsion/solvent extraction technique of the present invention, 500 mg of 50/50 poly(DL-lactide-co-glycolide) (PLGA, inherent viscosity 0.61 dL/g in HFIP at 30° C.) (Birmingham Polymers, Birmingham, Ala.) and 5 mg of polyethylene glycol (PEG; Mw: 4600) (Aldrich, Milwaukee, Wis.) were dissolved in 2 mL of methylene chloride (Fisher, Fair Lawn, N.J.) creating a 25% (w/v) solution. PEG was added to increase the degradation rate of the microspheres.

After allowing the polymers to dissolve, 100 mg of bovine serum albumin (BSA) powder (Sigma, St. Louis, Mo.) were added to the polymer solution and vortexed vigorously (Fisher, Fair Lawn, N.J.) at a medium-high setting for 30 seconds. Immediately, 10 mL of 0.3% (w/v) polyvinyl alcohol (PVA) were added to the protein—polymer solution and vortexed vigorously at a medium-high setting for an additional 30 seconds. The emulsion was added to a beaker containing an additional 90 mL of 0.3% PVA and 100 mL of 2% isopropyl alcohol and continuously stirred for 90 minutes at room temperature, allowing the organic solvent to be extracted from the polymer—protein complex. The resultant microspheres were centrifuged and washed in distilled water multiple times, frozen to −80° C., and lyophilized. For the degradation study, control microspheres containing no protein were fabricated using the same methodology. Microspheres containing rhVEGF165 (R&D Systems, Minneapolis, Minn.) were manufactured by coencapsulating the VEGF with BSA. Two different ratios of VEGF—BSA (w/w) were manufactured and characterized: 1:2000 and 1:10,000 (i.e., 50 and 10 mg of VEGF were added to the 100 mg of BSA, respectively).

Loading Efficiency

The loading efficiency, or the ratio of BSA encapsulated in the PLGA microspheres to the initial mass of BSA, was determined by dissolving 20 mg of the microspheres in 1 mL of 1N NaOH (Sigma) overnight and measuring the absorbance at 284 nm on a spectrophotometer (Beckman Instruments, Fullerton, Calif.) and compared to a standard curve. The results are expressed as a percentage of the ratio of protein encapsulated to total protein used.

Particle Size Distribution and Bright-Field Imaging

To determine the degree of uniformity between manufactured lots, the particle size distribution (PSD) was measured. A random sample of microspheres was resuspended in water, mounted on a microscope slide, and visualized by bright-field light microscopy (Olympus, Melville, N.Y.). Multiple low-power fields were imaged using a 24-bit color CCD video camera (Hamamatsu, Bridgewater, N.J.). The particle diameters were measured using image-processing software (IPLab, Scanalytics, Billerica, Mass.) calibrated to the video microscopy system.

Individual microspheres were imaged at high-power by bright-field light microscopy to assess their morphology and internal structure. In addition, individual microspheres were optically sectioned using a computer-controlled microscope stage (Ludl Electronics, Hawthorne, N.Y.) and image-processing software (IPLab; Scanalytics, Billerica, Mass.).

Scanning Electron Microscopy

Samples for scanning electron micrographs were obtained on days 0, 7, 14, 21, and 28 to illustrate physical degradation and to assess the surface morphology of the microspheres over time. Samples were frozen to −80° C. and lyophilized. The lyophilized samples were mounted on carbon disks attached to aluminum scanning electron microscopic blocks, and sputter-coated with platinum/palladium particles followed by carbon particles. The blocks were mounted in a scanning electron microscope (Jeol JSM-5900, Peabody, Mass.) at 5 kV and imaged at ×200 and ×1000.

Release Kinetics of the VEGF/BSA Microspheres

Cumulative release kinetic studies were conducted to determine the temporal release of rhVEGF165 from the microspheres. Using sterile technique, 125 mg of rhVEGF165-loaded microspheres were placed into a 15-mL polystyrene conical tube (Falcon, Franklin Lakes, N.J.) with 5 mL of sterile PBS-Ab. PBS-Ab consisted of PBS containing 100 U/mL penicillin, 100 mg/mL streptomycin, and 292 mg/mL L-glutamine (Gibco BRL, Gaithersburg, Md.). The tubes were sealed and placed in a 37° C. incubator (Nuaire, Plymouth, Minn.) on a shaker table (Fisher) to ensure continuous mixing. Every 4 days the samples were removed from the incubator and centrifuged (Jouan, Winchester, Va.) at 200×g for 10 min.

Using sterile technique, 2.5 mL of the supernatant was removed and reserved in a new labeled tube. The removed solution was replaced with an equal volume of fresh sterile PBS-Ab. The sample tubes containing microspheres were returned to the shaker table in the 37° C. incubator until the next time point. The reserved supernatant was stored at −80° C. until it was analyzed. Analysis of the thawed supernatant from the microspheres was conducted using an enzyme-linked immunosorbent assay (ELISA) specific for rhVEGF165 (R&D Systems, Minneapolis, Minn.). Concentrations of VEGF were determined by comparison to a standard curve. All analyses were conducted in duplicate.

Human Umbilical Vein Endothelial Cell (HUVEC) Culture

Human umbilical vein endothelial cells (Clonetics, Walkersville, Md.) were cultured in T-25 cell culture flasks (Falcon). The culture medium, endothelial cell growth medium-2 (EGM-2; Clonetics, Walkersville, Md.), is a proprietary basal media supplemented with human recombinant epidermal growth factor, human basic fibroblast growth factor, VEGF, ascorbic acid, hyrdocortisone, human recombinant insulin-like growth factor, heparin, 5% fetal bovine serum, gentamicin, and amphotericin. The HUVECs were incubated at 37° C. in a 5% $CO_2$/95% air, 95% humidity incubator (Nuaire, Plymouth, Minn.) Culture media were changed every other day and the cells were subcultured when 80-90% confluency was achieved.

Bioactivity of Released VEGF

The bioactivity of the released VEGF was evaluated in vitro using a HUVEC proliferation assay as described by Visweswaran P., et al., "Stimulation of Growth and Migration of Vascular Endothelial Cells by Vascular Endothelial Growth Factor Transduced Smooth Muscle Cells in Co-culture," ASAIO J. 1997, 43:M753-M758. Briefly, HUVECs were plated into tissue culture—grade 12-well plates at a density of 10,000 cells/well. To control for the effect of VEGF in the cultures, the EGM-2 was modified (mEGM-2) for these experiments by excluding the supplied VEGF from the media. The undiluted supernatant from the degradation of the VEGF microspheres was added to the mEGM-2, sterilized by membrane filtration (0.22 mm; Costar, Corning, N.Y.), and incubated with the HUVECs. The results of the VEGF ELISA were used to determine the concentration of VEGF within the supernatant.

There were five experimental groups: supernatant from BSA microspheres, supernatant from VEGF microspheres (final concentration of VEGF, 6 ng/mL), supernatant from empty microspheres, exogenous VEGF (final concentration, 6 ng/mL) (R&D Systems), and mEGM-2 alone. The mEGM-2 and supernatant from BSA and empty microspheres served as negative controls, whereas wells with exogenous VEGF added to the media served as positive controls. The exogenous VEGF or appropriate supernatant was added to the mEGM-2 and sterilized by membrane filtration with each media change.

To control for the media dilution effect associated with adding the supernatants, the mEGM-2 alone and exogenous VEGF media were supplemented with an equal volume of PBS-Ab. Media changes occurred every other day. HUVECs received EGM-2 on day 0 and the appropriate experimental media on days 2 and 4. The growth curves conducted in triplicate over 6 days were evaluated for increased proliferation of the HUVECs by trypsinization of the cells on days 0, 2, 4, and 6 and cell counting using a Coulter counter (Coulter Corp., Miami, Fla.).

Data Interpretation

Statistical significance was calculated using one-way analysis of variance (ANOVA) with Tukey—Kramer multiple comparisons post test. Statistical significance was defined as $p \leq 0.05$.

Microsphere Production, Loading Efficiency, and Particle Size Distribution

FIG. 1(A) is an image of a large microsphere of the present invention viewed under bright-field microscopy. Microdomains are discernable within the microsphere. The black bar represents 20 mm. FIG. 1(B) is an image of small microspheres of the present invention viewed under bright-field microscopy. The small microspheres of FIG. 1(B) appear more homogeneous than the large microspheres of which that shown in FIG. 1(A) is an example. The black bar represents 20 mm. The small microspheres of FIG. 1(B) are from the same population. Generally, FIGS. 1(A) and (B) reveal that microspheres of the present invention appeared spherical in shape and that large microspheres produced by the present invention contain several internal microdomains, whereas small microspheres produced by the present invention have a more homogeneous appearance.

The amount of encapsulated protein was determined by dissolving microspheres in NaOH. The loading efficiency using this technique was calculated to be 16.00±0.96% [mean±standard error of the mean (SEM)].

Figure 2:
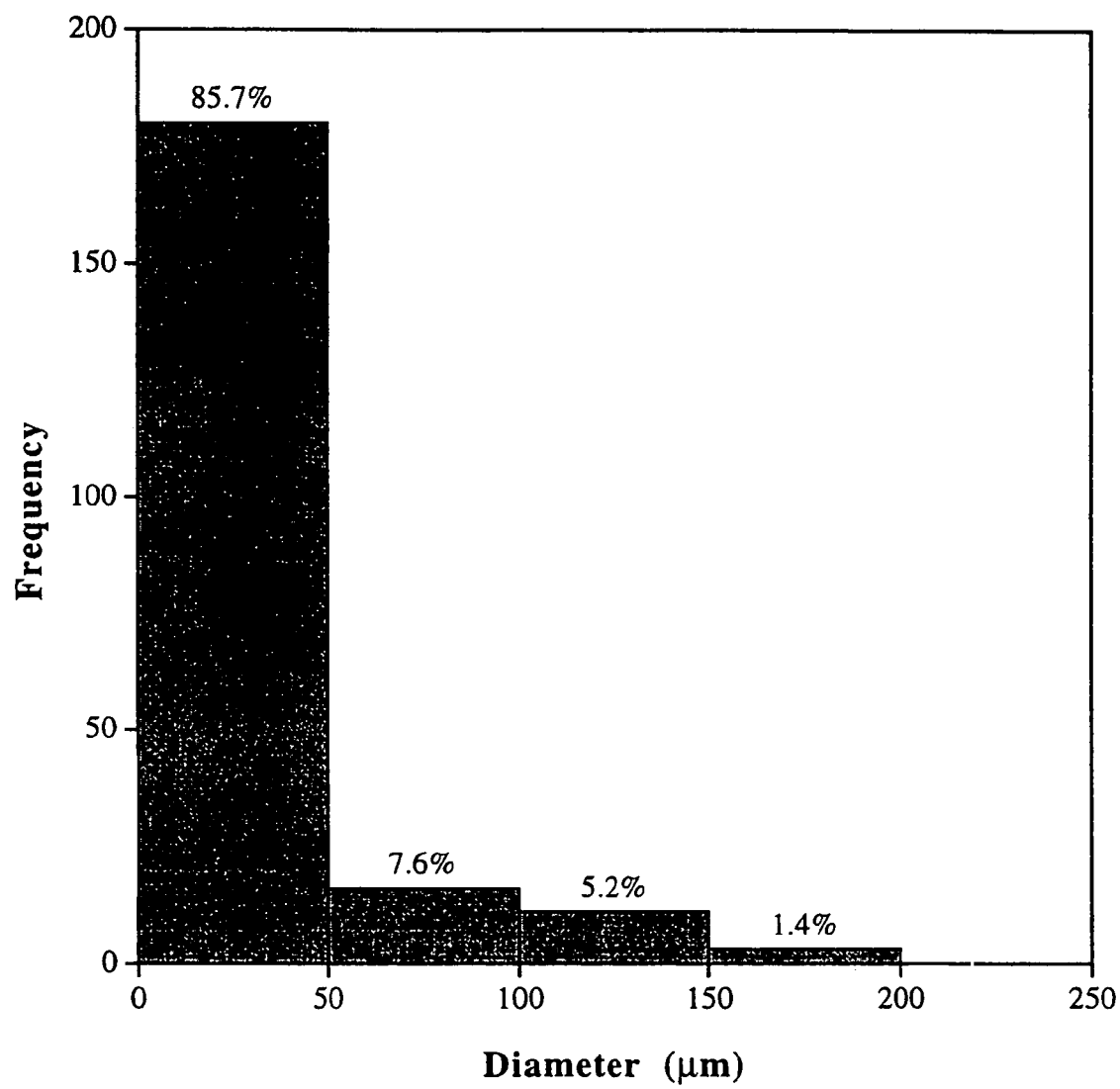
FIG. 2 is a histogram of particle size distribution of microshperes of the present invention.

FIG. 2 is a particle size distribution histogram showing a representative particle size distribution for microspheres of the present invention. The majority of the microspheres are in the size range of 0-50 μm in diameter. All lots demonstrated consistent histograms. All microsphere lots of the present invention produced consistent size-distribution histograms and displayed similar characteristics.

Scanning Electron Microscopy

FIGS. 3A through 3J show scanning electron micrographs of degrading microspheres. (A, B) Day 0, (C, D) day 7, (E, F) day 14, (G, H) day 21, (I,J) day 28. Note the smoothness of the microspheres on day 0. As the microspheres degrade, they decrease in size and meld together. Top row (FIGS. 3A, C, E, G, I):original magnification=×200, bars denote 100 mm; bottom row (FIGS. 3B, D, F, H, J) original magnification=×1000, bars denote 10 mm.

Figure 3:
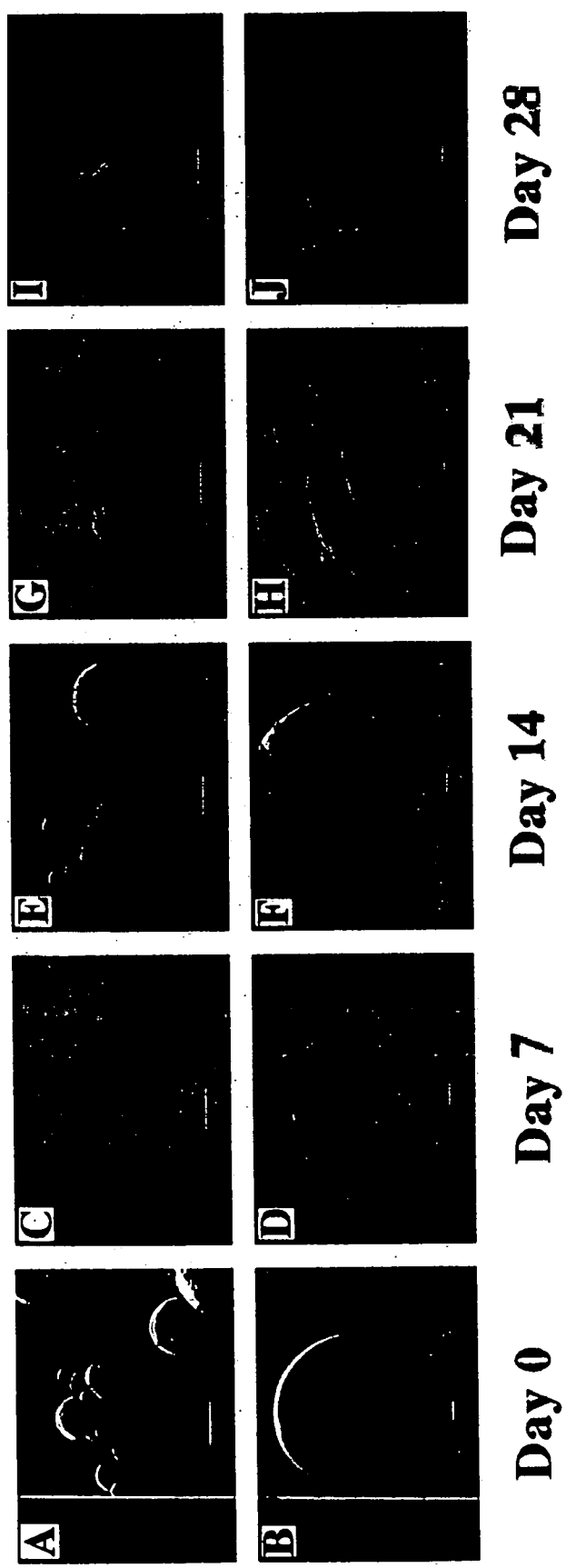
FIGS. 3A through 3J are scanning electron micrographs of degrading microspheres of the present invention.

The surface morphology of the microspheres was determined by SEM analysis for each time point. As shown in FIGS. 3(A) and (B), the surface morphology of the day 0 microspheres was smooth. As time progressed, the microspheres degraded and the surface became rough. In addition, as they degraded, the smaller microspheres appeared to meld with larger ones, e.g., FIG. 3(F). By day 28 the microspheres degraded to an extent that all spherical morphology was lost. FIGS. 3(I) and (J).

Release Kinetics of VEGF/BSA Microspheres

Figure 4:
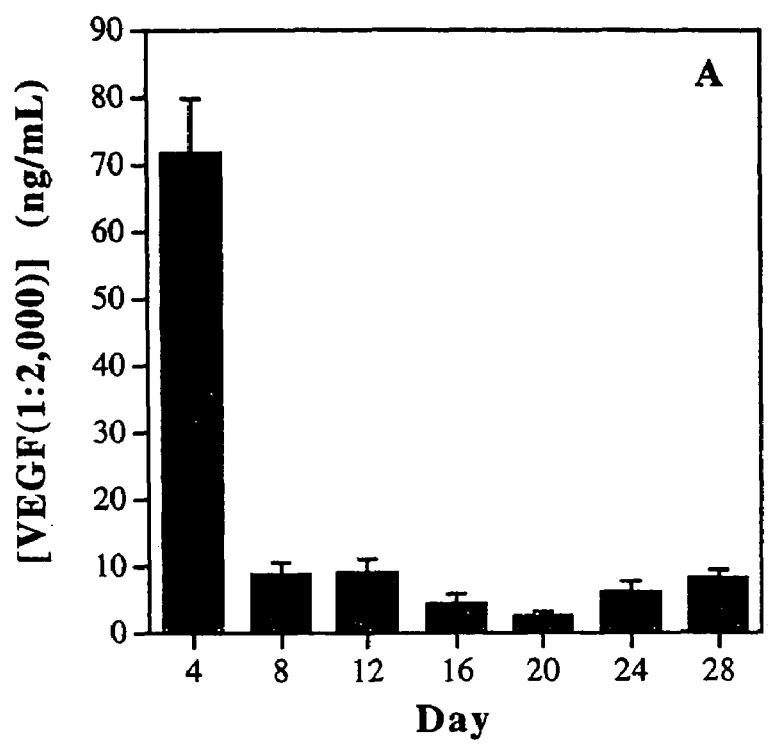
FIG. 4(A) is a graph illustrating release kinetics of VEGF: BSA 1:2000 microspheres of the present invention.
FIG. 4(B) is a graph illustrating release kinetics of VEGF: BSA 1:10000 microspheres of the present invention.
Figure 4:
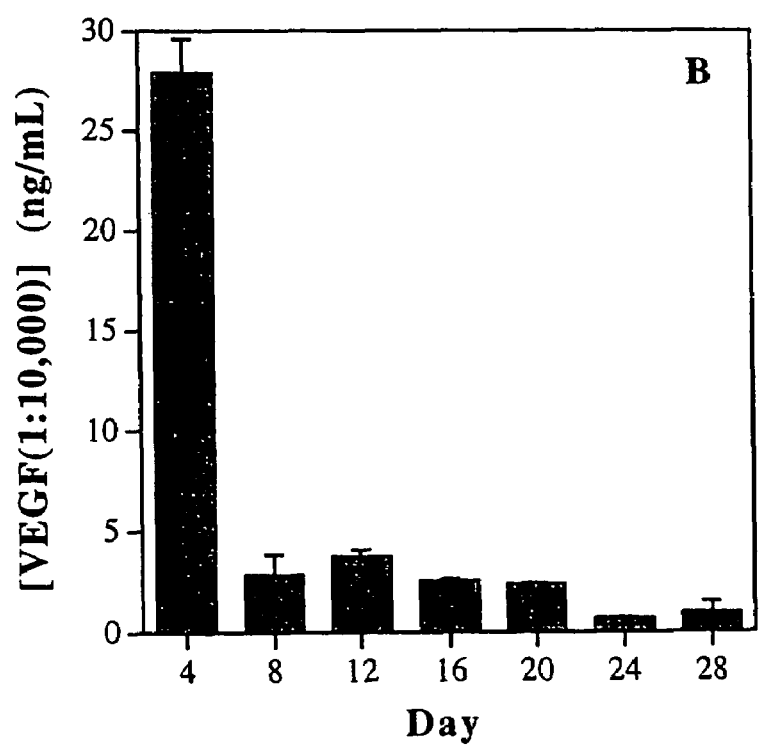

FIGS. 4A and 4B illustrate the release kinetic profiles for VEGF/BSA microspheres of the present invention. FIG. 4(A) shows the kinetics for a VEGF:BSA ratio of 1:2000. FIG. 4(B) shows the kinetics for a VEGF:BSA ratio of 1:10,000. Note the different scales on the y axis. In both cases the microspheres had an initial burst release followed by a lower steady-state release of 6.56±1.10 and 2.21±0.47 ng/mL (mean±SEM, n=4) for (A) and (B), respectively. The concentration of the steady-state release of the 1:2000 VEGF, FIG. 4(A), was in the physiologically active range of ED50: 2-6 ng/mL. After the initial burst, the 1:2000 VEGF microspheres released physiological levels of VEGF for at least 28 days.

Bioactivity of Released VEGF

Figure 5A:
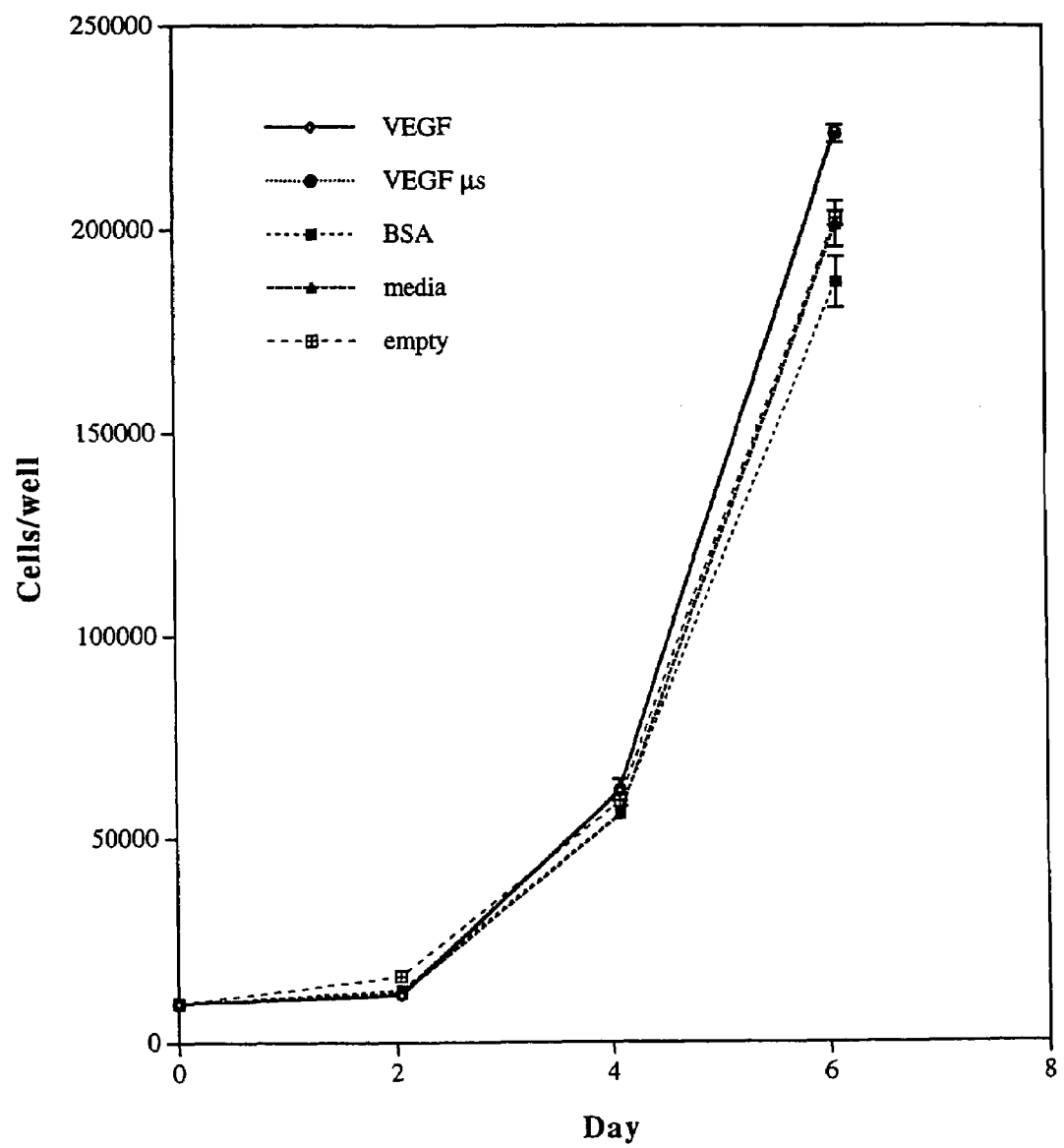
FIG. 5A is a graph of a growth curve of cell proliferation including cells exposed to VEGF microspheres of the present invention.
Figure 5B:
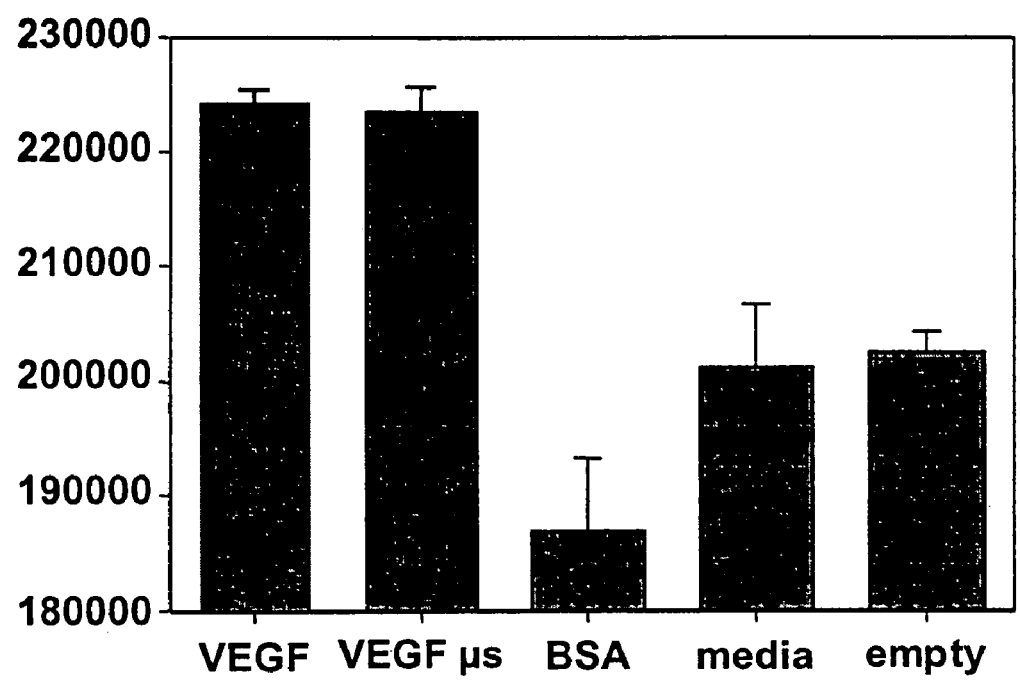
FIG. 5B is a histogram depiction of the graph of FIG. 5A

FIGS. 5A and 5B depict the growth curve for the HUVEC proliferation assay. FIG. 5A illustrates the data in graphical form and FIG. 5B illustrates the data in hisotgram form. The legend is the same for both figures and refers to the supplemental media each group received, and is as follows: VEGF=exogenous VEGF added to the media; VEGF ms=supernatant from degraded VEGF microspheres; BSA=supernatant from degraded BSA microspheres; media=mEGM-2 media alone (without VEGF); empty=supernatant from degraded empty microspheres. The exogenous VEGF served as a positive control, whereas the media alone, BSA microsphere supernatant, and empty microsphere supernatant served as negative controls. The cells treated with VEGF and VEGF microsphere supernatant had a faster rate of proliferation compared to the negative controls. The data represent mean±SEM of three experiments.

The bioactivity of the VEGF released from the microspheres over time was assessed using an in vitro HUVEC proliferation assay. Endothelial cells responded to bioactive VEGF by proliferating and migrating. The results of the assay are shown as a growth curve in FIG. 5A and as a histogram in FIG. 5B. The cells exposed to exogenous VEGF or supernatant from VEGF microspheres showed an increased rate of proliferation as indicated by an increased number of cells per well at days 4 and 6 ($p<0.05$ for day 6) compared to the negative controls. In addition, the VEGF from the microsphere supernatant was as potent as exogenously added VEGF. That is, 6 ng/mL of VEGF microsphere supernatant=6 ng/mL of exogenous VEGF.

In summary, sustained delivery of polypeptides is possible through the use of biodegradable microspheres. PLGA is a polymer that has been used for many years as a biodegradable suture material. PLGA is biocompatible and degrades by hydrolytic cleavage into nontoxic molecules that are easily eliminated from the body (namely, lactic acid and glycolic acid). In addition, PLGA has been described as a desirable polymer for use as a drug delivery system. Previous investigators have attempted to incorporate polypeptides into PLGA microspheres with variable success. Some of the polypeptides used include nerve growth factor, interferon, growth hormone, insulin, erythropoietin, transforming growth factor, epidermal growth factor, interlukin-2, basic fibroblast growth factor, and VEGF.

In the present invention, biodegradable PLGA/PEG microspheres were used to develop a system capable of releasing bioactive proteins. The encapsulation efficiency (16.00±0.96%) was consistent with previously published results for 50/50 PLGA (14.5±1.06). The VEGF encapsulated and released from the microspheres retained its biological activity in vitro.

The most commonly reported method for the manufacturing of microspheres is the double-emulsion technique. In this process, the protein is dissolved in an aqueous solution, which is then emulsified in an organic solvent containing the dissolved PLGA. The aqueous-organic emulsion is then further emulsified in an aqueous alcohol phase, creating an aqueous-organic-aqueous double emulsion. Over the course of approximately one hour, the alcohol phase extracts the organic solvent away from the PLGA, leaving the protein entrapped in discrete droplets within solid microspheres. However, the process of emulsifying the aqueous protein solution in the organic solvent may denature the protein. In the hands of the present inventors, the double emulsion method yielded inactive VEGF (data not shown). Iwata, et al., observed similar results in that TNF could not be incorporated into PLGA microspheres using the double-emulsion technique without marked activity loss of TNF by the organic solvent. Iwata M., Tanaka T., Nakamura Y., McGinity J. W., "Selection of the Solvent System for the Preparation of Poly(d,l Lactic-co-glycolic Acid) Microspheres Containing Tumor-necrosis Factor-alpha (TNF)," Int. J. Pharm. 1998; 160:145-156; and Iwata M., et al., "Particle Size and Loading Efficiency of Poly(d,l-lactic-co-glycolic Acid) Multiphase Microspheres Containing Water Soluble Substances Prepared by the Hydrous and Anhydrous Solvent Evaporation Methods," J. Microencapsulation 1999; 16:49-58.

Without a stabilizing agent the protein acts as a surfactant. Several stabilization methods have been attempted, with variable success. These methods include maximizing the protein concentration in solution, adding a metal (e.g., zinc), adding an additional carrier protein (e.g., albumin), adding gelatin, or adding a small osmolyte such as trehalose or mannatol. All of these stabilization methods, however, are used with aqueous protein solutions and are not completely effective in protecting the bioactivity of the released protein.

Another manufacturing process, the atomization-freeze process (AF), is commonly used for solid protein encapsulation. The AF process requires an ultrasonic atomizer with a custom-designed spray nozzle. Techniques that use solid proteins, as opposed to aqueous protein solutions, have shown higher protein integrity and efficiencies, both during encapsulation and upon release. Therefore, a combination of the double-emulsion technique and the AF process into a unique solid-encapsulation/single-emulsion/solvent extraction method is hereby provided for the microencapsulation and controlled delivery of polypeptides or other therapeutic agents in solid form with useful bioactivity.

In the VEGF example described above, BSA was used as a carrier protein. The addition of BSA aids in protecting the growth factor from denaturing in organic solvents.

The method described here is similar to the solid-encapsulation method recently reported by Cao and Shoichet with a few notable exceptions. First, the present invention uses a polymer blend of PLGA/PEG, whereas Cao and Shoichet used PLGA alone or PLGA/poly(-caprolactone). For instance, in the present example a 50/50 PLGA/PEG blend was selected based on the desire to have complete degradation by 4 weeks. The release kinetics were determined, in part, by the amount of drug loaded, the type of polymer used, and the manufacturing conditions. Particle size was determined by manufacturing conditions (e.g., solution viscosity, vortexer speed). Smaller particles had a faster degradation rate owing to the increased surface area to volume ratio. In addition, when the protein/polymer ratio is low (ratio=0.198 in system described here), the release of proteins from PLGA microspheres is generally regulated by the rate of physical erosion of the polymer shell of the microsphere.

The second, and most significant, difference in the present invention compared to Cao and Shoichet is the use of an inexpensive vortexer for the production of the single emulsion. Cao and Shoichet used a tissue homogenizer to produce the emulsions. When considering the scalability of a manufacturing process, a vibrating method is easier to scale than a homogenizer with variable generators (heads) and RPM settings. Furthermore, with the vortexer, sterility may be maintained throughout the entire manufacturing process without the need to clean and resterilize equipment between each batch. The present invention offers a less expensive alternative to the technique of Cao and Shoichet.

The successful development of a delivery system for therapeutic agents including polypeptides requires the preservation of the biological function of the agent at physiological concentrations. In the present example, the VEGF released from the microspheres was detected via ELISA and maintained in vitro bioactivity as demonstrated by the HUVEC proliferation assay. The concentrations of VEGF used are consistent with values found in physiological conditions of angiogenesis. Furthermore, the released VEGF maintained the same potency for endothelial cell proliferation as the exogenous VEGF added to the positive control. The example demonstrates that with the solid-encapsulation/single-emulsion/solvent extraction method of the present invention, VEGF may be encapsulated, stored, and released from biodegradable PLGA/PEG microspheres without a significant loss of function in vitro.

Although the invention has been described in connection with specific embodiments, it should be understood that the invention as claimed should not be unduly limited to such specific embodiments. Modifications and variations of the described compositions and methods of the invention will be apparent to those skilled in the art without departing from the scope and spirit of the invention. Indeed, various modifications of the described compositions and modes of carrying out the invention which are obvious to those skilled in molecular biology or related arts are intended to be within the scope of the following claims.

What is claimed is:

1. A system for delivering a therapeutic agent to a subject, the system comprising:
biodegradable microspheres comprising a biodegradable polymer and a biologically effective amount of a polypeptide therapeutic agent having usefully preserved bioactivity, wherein the microspheres are obtained from a single emulsion of the biodegradable polymer, the polypeptide therapeutic agent, and an organic solvent, the method comprising:
dissolving the biodegradable polymer with an organic solvent to produce a polymer solution;
adding the polypeptide therapeutic agent to the polymer solution to produce a mixture of polymer and polypeptide therapeutic agent, wherein no additional processing medium is required;
vibrating the mixture to produce a polypeptide therapeutic agent-polymer complex;
emulsifying the mixture to produce an emulsion comprising the polypeptide therapeutic agent-polymer complex; and
extracting the organic solvent from the emulsion to produce microspheres comprising the polypeptide therapeutic agent-polymer complex, wherein no additional emulsification or mechanical agitation is performed; and a means for delivering the microspheres to the subject in need thereof.

2. The system of claim 1, wherein release occurs in two phases selected from the group consisting of an initial burst phase and a later steady-state phase.

3. The system of claim 1, wherein the microspheres further comprise one or more biodegradable polymers.

4. The system of claim 1, wherein the microspheres further comprise one or more stabilizers selected from the group consisting of protein, metal, gelatin, and small osmolyte.

5. The system of claim 1, wherein the method further comprises washing, freezing and lyophilizing the microspheres.

6. The system of claim 1, wherein the polypeptide therapeutic agent is a drug.

* * * * *